United States Patent [19]

Abe

[11] Patent Number: 5,183,049

[45] Date of Patent: Feb. 2, 1993

[54] METHOD FOR FORMING AND ULTRASONIC IMAGE

[75] Inventor: Toshihiko Abe, Tagajou, Japan

[73] Assignee: Japan as represented by Director General of Agency of Industrial Science and Technology, Tokyo, Japan

[21] Appl. No.: 775,558

[22] Filed: Oct. 15, 1991

[51] Int. Cl.5 ............................................... A61B 8/00
[52] U.S. Cl. ................................. 128/663.01; 73/642
[58] Field of Search ...................... 128/663.01, 662.03; 73/642, 644; 310/334, 335

[56] References Cited

U.S. PATENT DOCUMENTS 4,880,012  11/1989  Sato .................................. 128/663.01
5,025,790   6/1991  Dias ................................. 128/662.03
5,060,201  10/1991  Ishikawa et al. ................. 73/642 X

OTHER PUBLICATIONS

"Ultrasonic Diagnostic Apparatus" PCT/JP88/00660 published 12 Jan. 1989 as WO89/00026.

*Primary Examiner*—Francis Jaworski
*Attorney, Agent, or Firm*—Wenderoth, Lind & Ponack

[57] ABSTRACT

An improved method is proposed for the image information of a body by ultrasonic scanning in which the resolution of the image can be greatly improved without sacrifice in the penetrability of the ultrasonic waves, i.e. without increasing the ultrasonic frequency, into the body under inspection.

The improvement comprises:

attaching a central ultrasonic absorber to the ultrasonic objective lens of the ultrasonic probe; and inserting an auxiliary concave lens between the ultrasonic probe and the body under inspection.

4 Claims, No Drawings

METHOD FOR FORMING AND ULTRASONIC IMAGE

BACKGROUND OF THE INVENTION

The present invention relates to a method for forming an ultrasonic image in a non-destructive ultrasonic scanning inspection of a body to detect a defect inside thereof. More particularly, the invention relates to a method for forming an ultrasonic image having increased sharpness with improved resolution.

The ultrasonic imaging method is widely practiced in many fields including the medical technology, in which a direct-contact probe is used, with an object to visually detect any defect or abnormality in the body of a patient at a desired depth from the skin surface. The ultrasonic imaging method is performed by scanning a beam of ultrasonic waves in place of light or X-rays to form an image. Like other imaging methods, the resolution of images formed by the ultrasonic imaging method is improved as the frequency of the ultrasonic waves is increased although this improvement in the resolution is obtained at the sacrifice of penetration of the ultrasonic beams into the body as a consequence of the increase in the scattering and absorption of the ultrasonic energy. For example, so called ultrasonic microscopes, which utilize ultrasonic waves having an extremely high frequency of 1 GHz or higher, can be used only for the inspection of the very surface layer of the body having a thickness of as small as a few $\mu$m due to absorption of the ultrasonic waves by the body although the ultrasonic image of the surface layer obtained with an ultrasonic microscope has a resolution comparable to that obtained with an optical microscope.

When the frequency of the ultrasonic waves is decreased to several MHz as in the conventional ultrasonic inspection method, the problem of the ultrasonic attenuation is no longer a limiting factor of the method but the resolution of the image is decreased so greatly that details of the inner structure of the body can hardly be visually inspected.

In most of ceramic materials, composite materials, integrated circuits and the like as an objective of the ultrasonic inspection method, on the other hand, it is sufficient in most cases that the ultrasonic beams reach a depth of a few millimeters from the surface so that ultrasonic waves having a frequency of several tens of MHz are satisfactory in respect of the balance between penetrability of the beams and resolution of the image.

Thus, it is important and eagerly desired to develop a method for improving the resolution of the ultrasonic images in the ultrasonic inspection method without sacrifice in the penetrability of the ultrasonic beams in the frequency region from a few MHz to several tens of MHz.

SUMMARY OF THE INVENTION

An object of the invention accordingly is to provide a novel method for improving the resolution of an ultrasonic image in the ultrasonic inspection method without sacrifice in the penetrability of the ultrasonic beams into the body under inspection or, namely, without increasing the frequency of the ultrasonic waves.

Thus, the method of the present invention for the ultrasonic image-formation of a body under inspection by scanning the body with an ultrasonic beam emitted from an ultrasonic probe comprises:

attaching a central ultrasonic absorber to the objective ultrasonic lens of the ultrasonic probe; and inserting an auxiliary concave lens between the ultrasonic probe and the body under inspection.

DETAILED DESCRIPTION OF THE PREFERRED EMBODIMENTS

The so-called resolution of an ultrasonic image includes the resolution in the horizontal direction or azimuthal resolution within the plane perpendicular to the ultrasonic beam expressed by $\Delta x$ and the depth resolution in the direction of the ultrasonic beam expressed by $\Delta z$. The improvement obtained by the inventive method is solely relative to the azimuthal resolution $\Delta x$ since the depth resolution $\Delta z$ is determined by the design of the electronic circuit.

It is known that, assuming that the objective ultrasonic lens of the ultrasonic Probe is free from any aberration, the azimuthal resolution $\Delta x$ is given by the equation $$\Delta x = \lambda/2 \sin \theta,$$

which $\lambda$ is the wavelength of the ultrasonic waves and $\theta$ is a half of the angular aperture of the objective ultrasonic lens of the probe relative to the point to be scanned by the ultrasonic beam, which is given by $\tan\theta = D/2L$, D and L being the diameter of the objective ultrasonic lens and the focal length, respectively, of the ultrasonic probe. The above given equation indicates that, assuming that the wavelength of the ultrasonic waves is the same, a smaller value of the resolution $\Delta x$ can be obtained by using an objective ultrasonic lens having a larger diameter to give a larger angular aperture. On the other hand, it is unavoidable that an ultrasonic lens having a larger angular aperture is accompanied by an increased spherical aberration as a consequence of the increased difference in the focal length between the center and the periphery of the lens resulting in poor focusing of the beam or an increased diameter of the beam at the focal point with a consequently decreased resolution of the image.

As is described above, the scope of the inventive method consists in attaching a central ultrasonic absorber to the objective ultrasonic lens of the ultrasonic probe and inserting an auxiliary concave lens between the ultrasonic probe and the body under inspection. The above mentioned central ultrasonic absorber attached to the objective ultrasonic lens is a small piece of disc made from various solid materials having a thickness of 0.1 to 1.0 mm and capable of absorbing ultrasonic waves. For example, satisfactory ultrasonic absorbers in the form of a small disc can be prepared by cutting or punching a pressure-sensitive adhesive plastic sheet provided that the sheet has a relatively large thickness of, for example, 0.5 mm or larger. Thin rubber sheets having a thickness of 0.5 to 1.0 mm can also be used for the purpose. When the central ultrasonic absorber is attached to the center of the ultrasonic lens of the probe, the ultrasonic waves emitted from and received by the probe pass through the ultrasonic lens only in the peripheral portion of the lens so that resolution of the ultrasonic image formed thereby can be improved as in the use of an ultrasonic lens having a larger angular aperture with a decreased spherical aberration. Although the sensitivity in the image formation is decreased as a consequence of the decrease of the area effective for penetration of the ultrasonic waves, the above mentioned advantage in the improvement of the resolution is more than sufficient to compensate for the disadvantage of the decrease in the sensitivity. The size of the central ultrasonic absorber should be selected in consideration of various factors such as the material of the body under inspection, depth of the part of which an ultrasonic image is desired and so on. When the size thereof is too small, no substantial improvement can be obtained in the resolution of the ultrasonic image while sensitivity of image formation would be decreased when the central ultrasonic absorber attached to the ultrasonic objective lens of the probe is too large. Usually, the central ultrasonic absorber has a diameter which is from 20 to 50% of the diameter of the ultrasonic objective lens in the probe.

Japanese Patent Kokai 1-260358 discloses an ultrasonic probe capable of giving improved resolution of the ultrasonic image by providing a void recess at the center of the flat surface of the ultrasonic objective lens with the flat surface facing the piezoelectric element. In this model of the probe, the void recess in the ultrasonic lens serves as an absorber of the ultrasonic waves so that only the portion of the ultrasonic waves passing through the peripheral zone of the lens having a large angular aperture is utilized for image formation. Such an ultrasonic probe, however, is not advantageous in practice because of the troublesomeness of working on the ultrasonic lens and poor versatility of the lens to a variety of objective bodies to be inspected.

In the second place, in the inventive method, an auxiliary concave lens is inserted between the ultrasonic objective lens of the probe and the body under inspection. The auxiliary concave lens can be attached to the objective lens of the probe or can be put on the body under inspection. The auxiliary concave lens is preferably a plano concave lens, especially when the concave lens is put on the body under inspection, with the flat surface facing the ultrasonic probe. The material of the concave lens is not particularly limitative including glass, plastic resins and the like. No optical transparency is required for the material so that metals and ceramics can also be used provided that the material is suitable for fabrication of the lens with good dimensional precision.

The term of "concave" lens is based on the form of the lens having the thickness smallest at the center of the lens increasing toward the periphery forming a spherical concave surface. In the technology of ultrasonics, the performance of a concave lens is analogous to that of an optical convex lens. Namely, the ultrasonic beam is imparted with an increased angular aperture by passing through a concave lens so that the resolution of the ultrasonic image can further be improved by the synergistic effect with the central ultrasonic absorber described above.

It is important for obtaining further improved resolution of the ultrasonic image by practicing the method of the invention to exactly focus the ultrasonic beam at the very point to be scanned. Following is a preferable procedure for the exact focusing. Assuming that the body under inspection is immersed in water, namely, the height of the end surface of the ultrasonic probe from the upper surface of the body under inspection, given by a symbol z, in mm should satisfy the equation $$z = -d \cdot v_2/v_1 + f + t,$$

in which f is the focal length in mm in water of the focusing system after correction with the auxiliary concave lens, t is the thickness in mm of the body under inspection, d is the depth in mm of the point to be imaged from the upper surface of the body and $v_1$ and $v_2$ are the velocities of sound in meters/second in water and in the body under inspection, respectively. In other words, the auxiliary concave lens to be inserted between the ultrasonic lens of the probe and the body under inspection should have a focal length with which the lens system consisting of the ultrasonic lens of the probe and the auxiliary concave lens has an overall focal length f satisfying the relationship given by the equation described above.

In the following, the method of the invention is described in more detail by way of an example. Example.

The body to be inspected in this example was the silicon chip in a resin encapsulated 40-pin integrated circuit, Model 6821, having dimensions of 52 mm by 14 mm by 4 mm. An ultrasonic mage of the silicon chip was taken in a photograph using an ultrasonic probe working at a frequency of 25 MHz, of which the ultrasonic objective lens had a diameter of 8 mm and a focal length in water of 9 mm. In a photograph taken with this ultrasonic probe as such, the arrangement of the wire-bonded portions at regular intervals around the silicon chip could barely be recognized. No improvement could be achieved in the resolution of the image for identifying details of the structure even by adjustment of various conditions so that the above taken photograph was considered to be the result of the best techniques available by using an ultrasonic frequency of 25 MHz.

In the next place, a small disc piece of 2.5 mm diameter was prepared from a pressure sensitive adhesive tape of 0.6 mm thickness and adhesively attached to the center of the ultrasonic lens of the probe. Concurrently, a 16 mm by 21 mm wide plano-concave lens made from a plastic resin having a focal length of 62 mm in air was put on the surface of the integrated circuit with the flat surface facing the ultrasonic probe and an ultrasonic image photograph was taken. The overall focal length of this system was 6 mm in water. This photograph indicated clearly recognizable 40 bonding wires distributed around a 3.2 mm square silicon chip at a regular pitch of 0.26 mm.

What is claimed is:

1. A method for the ultrasonic image-formation of a body under inspection by scanning the body with an ultrasonic beam emitted from an ultrasonic probe having an ultrasonic objective lens facing the body which comprises:

attaching a central ultrasonic absorber in the form of a disc to the center of the surface of the ultrasonic objective lens of the ultrasonic probe facing the body under inspection; and inserting an auxiliary concave lens between the ultrasonic objective lens of the ultrasonic probe and the body under inspection.

2. The method for the ultrasonic image-formation of a body under inspection as claimed in claim 1 in which the auxiliary concave lens is put on the surface of the body under inspection.

3. The method for the ultrasonic image-formation of a body under inspection as claimed in claim 2 in which the auxiliary concave lens is a plano-concave lens with the flat surface facing the ultrasonic objective lens of the ultrasonic probe.

4. The method for the ultrasonic image-formation of a body under inspection as claimed in claim 1 in which the central ultrasonic absorber has a thickness in the range from 0.1 to 1.0 mm and a diameter in the range from 20 to 50% of the diameter of the ultrasonic objective lens of the ultrasonic probe.

* * * * *